United States Patent [19]
Harder et al.

[11] Patent Number: 5,629,140
[45] Date of Patent: May 13, 1997

[54] PHOTOGRAPHIC ELEMENTS CONTAINING SCAVENGERS FOR OXIDIZED DEVELOPING AGENT

[75] Inventors: John W. Harder, Rochester; John V. Nelson, Penfield; Stephen P. Singer, Spencerport, all of N.Y.

[73] Assignee: Eastman Kodak Company, Rochester, N.Y.

[21] Appl. No.: 373,131

[22] Filed: Jan. 17, 1995

[51] Int. Cl.$^6$ .............................. G03C 1/34; G03C 1/43; G03C 7/392
[52] U.S. Cl. .................... 430/489; 430/598; 430/486; 430/214
[58] Field of Search .................................. 430/598, 486, 430/489, 214

[56] References Cited

U.S. PATENT DOCUMENTS

| | | | |
|---|---|---|---|
| 4,923,787 | 5/1990 | Harder | 430/489 |
| 4,971,890 | 11/1990 | Okada et al. | 430/264 |
| 5,147,764 | 9/1992 | Bowne | 430/372 |
| 5,164,288 | 11/1992 | Nelson et al. | 430/379 |
| 5,230,992 | 7/1993 | Miyahashi et al. | 430/505 |
| 5,360,702 | 11/1994 | Zengerle et al. | 430/505 |
| 5,468,592 | 11/1995 | Nii et al. | 430/264 |

FOREIGN PATENT DOCUMENTS

| | | | |
|---|---|---|---|
| 0723193 | 7/1996 | European Pat. Off. | G03C 7/392 |
| 4-238347 | 8/1992 | Japan . | |

*Primary Examiner*—Mark F. Huff
*Attorney, Agent, or Firm*—Alfred P. Lorenzo; J. Lanny Tucker

[57] ABSTRACT

An improved photographic element comprises a support bearing at least one silver halide emulsion layer having associated therewith a hydrazide compound that functions as a scavenger for oxidized developing agent. The hydrazide compound includes an electron-withdrawing and aqueous-solubilizing group on an aromatic ring linked to the carbonyl of the hydrazide group and a ballasting group on an aromatic ring linked to a nitrogen atom of the hydrazide group. Preferably, the hydrazide compound is incorporated in a photographic element which comprises a four-equivalent 5-pyrazolone magenta-dye-forming coupler.

24 Claims, No Drawings

PHOTOGRAPHIC ELEMENTS CONTAINING SCAVENGERS FOR OXIDIZED DEVELOPING AGENT

FIELD OF THE INVENTION

This invention relates in general to photography and in particular to photographic elements comprising at least one radiation-sensitive silver halide emulsion layer. More specifically, this invention relates to improved photographic elements containing compounds which act as scavengers for oxidized developing agent.

BACKGROUND OF THE INVENTION

It is known in the art to add a scavenger to a photographic element in order for the scavenger to prevent oxidized developing agent from reacting within the element at an undesired location or at an undesired point in time. In particular, it is undesirable for oxidized developer to diffuse away from the imaging layer in which it formed and into other color records where it can form dye in the wrong layer. In some formats, it can also be undesirable for toe scale and fog considerations to have oxidized developer form dye at early stages of development. Typically, scavengers reduce or eliminate oxidized developers without forming any permanent dyes and do not cause stains nor release fragments that have photographic activity. They are also typically rendered substantially immobile in the element by incorporation of an anti-diffusion group (a ballast) or by attachment to a polymer backbone.

Known scavengers for oxidized developers include ballasted hydroquinone (1,4-dihydroxybenzene) compounds as described in U.S. Pat. Nos. 3,700,453 and 4,732,845; ballasted gallic acid (1,2,3-trihydroxybenzene) compounds as described in U.S. Pat. No. 4,474,874; ballasted sulfonamidophenols as described in U.S. Pat. Nos. 4,205,987 and 4,447,523; and ballasted resorcinol (1,3-dihydroxybenzene) compounds as described in U.S. Pat. No. 3,770,431. Such known materials are insufficient in their activity, requiring high material usage, thus increasing cost, storage and handling concerns as well as requiring thicker layers, thus degrading sharpness through increased scatter path length. In addition, because these known materials are sensitive to oxidative conditions, they are often insufficiently stable upon long term storage. Finally, many of these materials form stains or colored residues during processing.

It is also known to use certain hydrazide compounds in color photographic elements as scavengers for oxidized developing agent. Thus, for example, U.S. Pat. No. 4,923,787 discloses the use of hydrazides of the formula

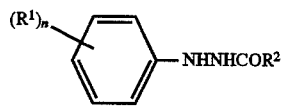

wherein $R^1$ is an electron-donating group, $R^2$ is hydrogen, alkyl, alkoxy, aryl, aryloxy, aralkyl or amino and n is 1 or 2; and Japanese Patent Publication No. 4,238,347, published August 26, 1992, discloses the use of hydrazides of the formula

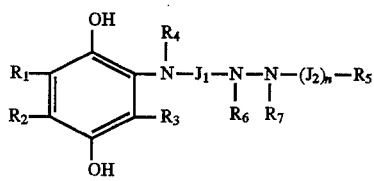

wherein $R_1$, $R_2$ and $R_3$ are hydrogen, halogen, alkyl, alkenyl, alkoxy, aryloxy, alkylthio, arylthio, acylamino, sulfonyl, carbamoyl, sulfamoyl or sulfo, $R_1$ and $R_2$ can connect to form a ring structure;

$R_4$, $R_6$ and $R_7$ are hydrogen or alkyl;

$R_5$ is alkyl, cycloalkyl, aralkyl, alkenyl, aryl or a hetero ring;

$J_1$ is —CO—, —SO— or —SO$_2$—;

$J_2$ is —CO—, —SO—, —SO$_2$—or —COCO—; and n is zero or one.

U.S. Pat. No. 4,971,890, issued Nov. 20, 1990, discloses photographic elements containing a hydrazide compound represented by the formula:

$$R_1-SO_2NH-Y_1-\overset{A_1}{\underset{|}{N}}-\overset{A_2}{\underset{|}{N}}-G_1-L_1-Z_1$$

wherein at least one of $A_1$ and $A_2$ represents a hydrogen atom and the other represents a hydrogen atom, a sulfonyl group or an acyl group; $R_1$ represents an aliphatic group, an aromatic group, or a heterocyclic group; $Y_1$ represents a divalent organic group; $G_1$ represents a carbonyl group, a sulfonyl group, a sulfoxy group,

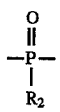

wherein $R_2$ represents an alkoxy group or an aryloxy group,

or an iminomethylene group; $Z_1$ represents a group suitable for making a nucleophilic attack on $G_1$ to separate the $G_1-L_1-Z_1$ from the rest of the molecule, and $L_1$ represents a divalent organic group suitable for producing a cyclic structure with $G_1$ and $Z_1$ upon. nucleophilic attack by $Z_1$ on $G_1$.

U.S. Pat. No. 5,147,764, issued Sep. 15, 1992, discloses the use of the hydrazide compounds described in U.S. Pat. No. 4,923,787 in photographic elements containing a two-equivalent 5-pyrazolone magenta-dye-forming coupler.

U.S. Pat. No. 5,164,288, issued Nov. 17, 1992, discloses the use of the hydrazide compounds described in U.S. Pat. No. 4,923,787 in photographic elements containing a pyrazoloazole magenta-dye-forming coupler.

U.S. Pat. No. 5,230,992, issued Jul. 27, 1993, discloses color photographic elements containing a hydrazide compound to reduce color staining and color fog. The compounds disclosed have the formula

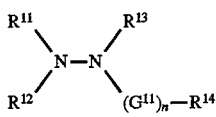

wherein $R^{11}$, $R^{12}$ and $R^{13}$ represent hydrogen, an aliphatic group or an aromatic group, $R^{14}$ represents hydrogen, an alkyl group, an aralkyl group, an aryl group, a heterocyclic group, an alkoxy group, an aryloxy group, an amino group, an alkoxycarbonyl group, an aryloxycarbonyl group or a carbamoyl group, $G^{11}$ represents a carbonyl group, a sulfonyl group, a sulfinyl group, a

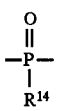

group, or an iminomethylene group, and n is 0 or 1.

The hydrazide compounds described above suffer from many of the same disadvantages and deficiencies as the hydroquinone, gallic acid, sulfonamidophenol and rescorcinol compounds. In particular, these hydrazide compounds are especially deficient in regard to activity and long-term storage stability.

It has also been found that the known hydrazide scavengers can produce undesired yellow dyes when used in photographic elements, particularly color reversal elements. These yellow dyes may arise solely from the hydrazide scavenger itself or from an interaction with four-equivalent 5-pyrazolone magenta-dye-forming couplers. Formation of either yellow dye results in inferior color reproduction. It is desirable to provide a hydrazide scavenger that avoids the formation of these unwanted yellow dyes without sacrificing either high activity or good storage stability.

It was not heretofore known that hydrazides which function as scavengers for oxidized developing agent were the source of a yellow dye stain problem. Thus, the present invention encompasses both the discovery of such problem and an effective solution to overcome the problem by structural modification of the hydrazide scavenger.

It is an objective of this invention to provide a new class of reactive scavengers for oxidized developer which can be incorporated in a wide range of photographic elements, and especially in color elements to prevent color contamination between layers, to prevent stain and to reduce fog. It is a particular objective of this invention to provide a new class of reactive scavengers that have high activity, that have excellent stability upon long-term storage and that do not leave colored residues after processing. It is a further particular objective of this invention to provide a new class of reactive scavengers that do not form unwanted yellow dyes, either alone or as a consequence of interaction with four-equivalent 5-pyrazolone magenta-dye-forming couplers.

SUMMARY OF THE INVENTION

In accordance with this invention, a photographic element comprises a support bearing at least one silver halide emulsion layer having associated therewith a hydrazide compound that functions as a scavenger for oxidized developing agent; wherein the hydrazide compound is represented by the following formula 1:

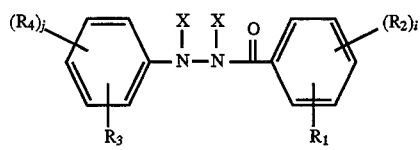

wherein:
each X is, independently, a hydrogen atom or a process-cleavable group;

$R_1$ is an electron-withdrawing and aqueous-solubilizing group;

each $R_2$ is, independently, a hydrogen atom or a monovalent organic substituent;

$R_3$ is a ballasting group;

each $R_4$ is, independently, a hydrogen atom or a monovalent organic substituent;

i is an integer with a value of 1 to 4, and j is an integer with a value of 1 to 4.

The groups X, $R_1$, $R_2$, $R_3$ and $R_4$ are described in greater detail hereinbelow.

DETAILED DESCRIPTION OF THE INVENTION

As hereinabove described, the present invention pertains to the use in silver halide photographic elements of certain hydrazide compounds which function as scavengers for oxidized developing agent.

Scavengers are compounds which react with oxidized developing agents by mechanisms such as cross-oxidation or coupling and deactivate the oxidized developing agent without forming permanent image. They can be incorporated within a silver halide emulsion layer to control curve shape. They can be incorporated within an interlayer to provide improved color reproduction.

The hydrazide compounds of this invention are highly effective scavengers which are utilized in association with a silver halide emulsion layer, by which is meant that they can be incorporated in a silver halide emulsion layer or in any other layer of a photographic element from which they can modify the characteristics of a silver halide emulsion layer.

Hydrazide scavengers are believed to react with oxidized developer by the mechanism shown in the following Scheme I.

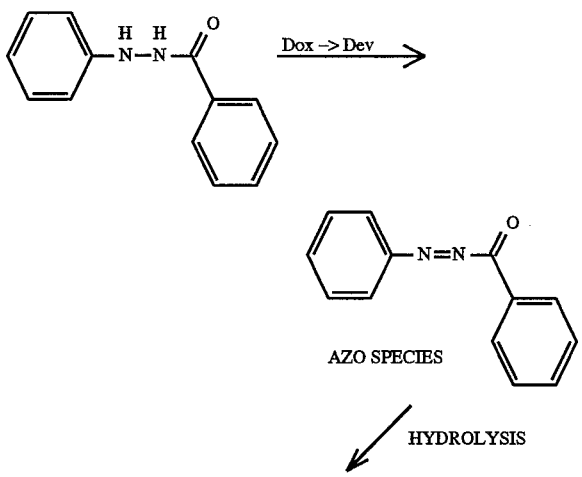

-continued

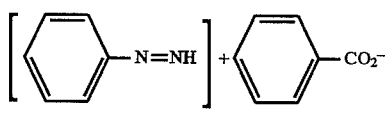

As shown in Scheme I, the scavenger is initially oxidized to an azo species. This azo species is a yellow dye and may cause an undesired stain if it is not hydrolyzed. Hydrolysis of the azo species forms two fragment residues: one derived from the hydrazine portion of the scavenger and one from the carboxylic acid portion of the scavenger. The fragment residue derived from the hydrazine portion of the scavenger will undergo a redox reaction with additional oxidized developer to form a more oxidized fragment residue. This more oxidized fragment residue may couple with four-equivalent 5-pyrazolone magenta-dye-forming couplers to form a second undesired yellow azo dye, may react with other components present in the photographic element, or may decompose to smaller fragment residues.

The scavengers of the present invention prevent the formation of stain from the yellow azo species shown in Scheme I by ensuring rapid hydrolysis of this species. Further, the scavengers of the present invention inhibit the formation of the second undesired yellow dye (formed by the reaction of the more oxidized fragment residue described above with four-equivalent 5-pyrazolone magenta-dye-forming couplers) by restricting the mobility of the fragment residue derived from the hydrazine portion of the scavenger. In addition, the scavengers of the present invention achieve these objectives without sacrificing either their high activity or good storage stability.

The above objectives are accomplished with a hydrazide scavenger represented by formula 1 above. The incorporation of the electron withdrawing and aqueous solubilizing group on the aromatic ring linked to the carbonyl of the hydrazide group facilitates the hydrolysis of the azo species in Scheme I. This hydrolysis is facilitated both by activation of the hydrazide carbonyl group through the electron withdrawing properties of the group and, particularly when the group is in an ortho position to the hydrazide carbonyl, by the presence of the solubilizing group near the hydrolysis reaction site. In addition, the solubilizing properties of the group increase the activity of the scavenger. The incorporation of the ballast group on the aromatic ring linked to the nitrogen of the hydrazide restricts the mobility of the fragment residue which is derived from the hydrazine portion of the scavenger in Scheme I. This inhibits the formation of yellow stain from the reaction of this fragment residue with four-equivalent 5-pyrazolone magenta-dye-forming couplers.

The X groups above, which may be the same or different, each represent hydrogen atoms or process-cleavable groups or one represents hydrogen and the other represents a process clearable group. A process-cleavable group is a group which undergoes a fragmentation or reaction breaking the bond between the group and the nitrogen atom of the hydrazide during the color development step of the photographic process or in one of the processing solutions prior to the color developer. Examples include $C_1$–$C_{30}$ alkylsulfonyl, $C_6$–$C_{30}$ arylsulfonyl and $C_1$–$C_{30}$ acyl groups. Preferably, the X groups may be hydrogen, alkylsulfonyl groups and arylsulfonyl groups which have not more than 20 carbon atoms (phenylsulfonyl and substituted phenylsulfonyl groups in which the sum of the Hammett substituent constants is at least −0.5 are more preferred), or acyl groups which have not more than 20 carbons (benzoyl, substituted benzoyl groups in which the sum of the Hammett substituent constants is at least −0.5, or linear chain, branched or cyclic unsubstituted or substituted aliphatic acyl groups which have, for example, halogen, ether, sulfonamido, carbonamido, hydroxyl, carboxyl, or sulfonic acid groups as substituent groups are more preferred). The X groups are most preferably hydrogen atoms.

The electron withdrawing and aqueous solubilizing group $R_1$ above is a group both with a Hammett sigma p value greater than 0.10 (the reference for all Hammett sigma p values herein is C. Hansch and A.J. Leo, *Substituent Constants for Correlation Analysis in Chemistry*, Wiley, New York, 1979) and with intrinsic hydrophilicity or the capability of substantial ionization under processing conditions. By intrinsic hydrophilicity is meant a group with a negative π coefficient (as reported by Hansch et al, *J. Med. Chem.*, 16, pp. 1207–1216, 1973). For ionizable groups, the Hammett sigma p value should correspond to the structure of the group at a pH value of 10 to simulate photographic processing conditions. Thus, while a carboxylic acid group has a Hammett sigma p value of 0.45, at a pH of 10 the group will be ionized to a carboxy anion which has a Hammett sigma p value of 0 (zero). Examples of the electron-withdrawing and aqueous solubilizing group, $R_1$, include aminosulfonyl (Hammett sigma p=0.62) and aminocarbonyl (0.36) groups. Preferably, the $R_1$ group is an aminosulfonyl group. It is also preferred that the $R_1$ group be in the ortho position to the carbonyl of the hydrazide to maximize its influence on the hydrolysis of the azo species in Scheme I through both electronic effects and, for some substituents, through anchimeric assistance of the hydrolysis reaction. Representative examples of the electron-withdrawing and aqueous-solubilizing group, $R_1$, are shown below.

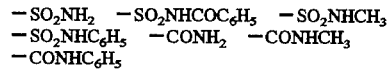

For group $R_3$ above, ballasting groups known in the art are suitable for the present invention. Preferably, they are groups which prevent substantial migration of the oxidized developer scavenger within the photographic element. Migration should be limited during both shelf keeping and processing. Preferably, the ballasting groups are large organic substituents containing at least 12, and more preferably at least 15, contiguous atoms and including substituted or unsubstituted alkyl, aryl or aralkyl groups. Representative substituents on such ballast groups include all those listed for substituent groups $R_2$ and $R_4$ below. Such substituents may also be further substituted. Representative examples of the ballast group, $R_3$, are shown below.

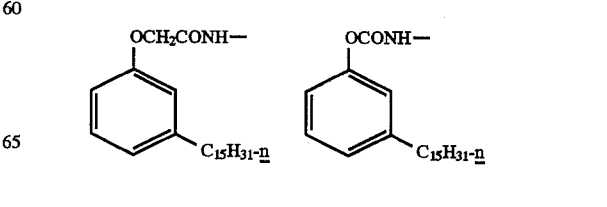

-continued

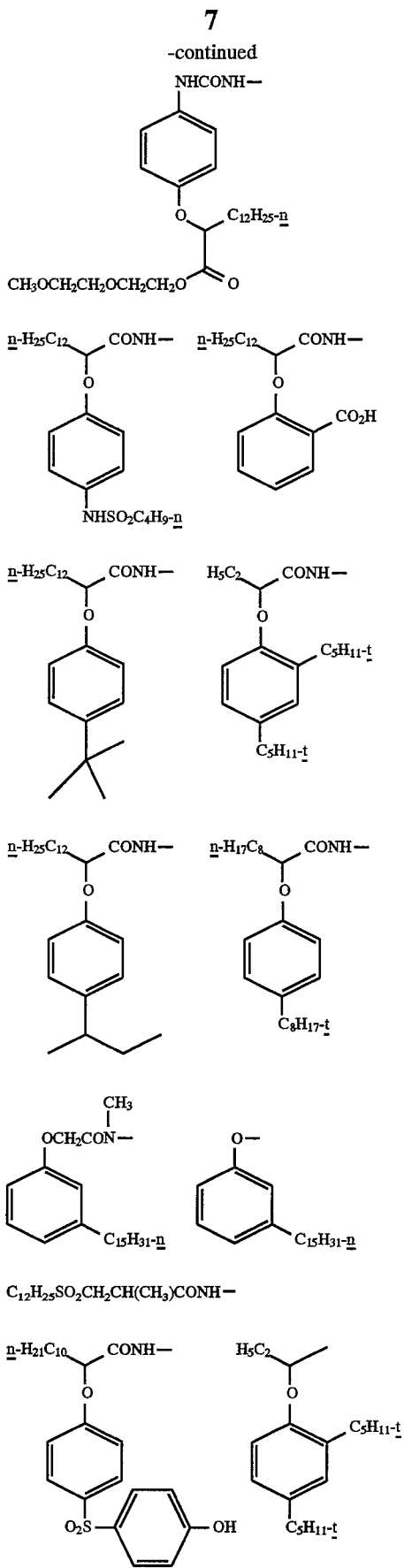

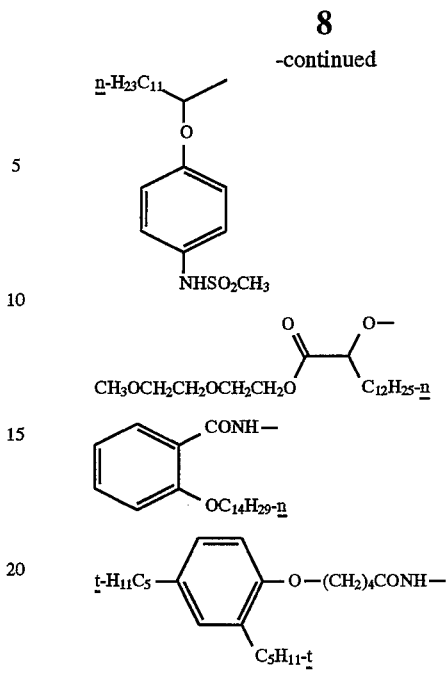

The aromatic ring linked to the carbonyl of the hydrazide may only be substituted with electron-withdrawing and aqueous solubilizing group $R_1$ (as defined above), the remaining four positions on the ring being occupied by hydrogen atoms, or it may be additionally substituted by one or more substituents $R_2$. Likewise, the aromatic ring linked to the nitrogen of the hydrazide may only be substituted with ballast group $R_3$ (as defined above) or it may be additionally substituted by one or more substituent groups $R_4$.

The substituent groups $R_2$ and $R_4$ above, which may be the same or different, may be alkyl, cycloalkyl, alkenyl, cycloalkenyl, alkynyl, aryl, heteroaryl, heterocyclyl, alkoxy, heterocyclyloxy, aryloxy, siloxy, alkylthio, arylthio, heterocyclylthio, hydroxy, halogen, cyano, nitro, alkoxycarbonyl, alkoxycarbonylamino, aryloxycarbonyl, aryloxycarbonylamino, aminocarbonyl, carboxy, acyl, acyloxy, amino, alkylamino, anilino, imido, ureido, carbonamido, carbamoyl, carbamoyloxy, sulfonyl, aminosulfonyl, sulfinyl, sulfonamido, sulfamoyl, sulfamoylamino, phosphenyl, spiro compound residues, bridged hydrocarbon residues, and the like. It is preferred that there be at least one $R_4$ substituent group and that this non-hydrogen substituent be an electron donating group with a Hammett sigma p value of 0 (zero) or less. Electron donating groups improve the activity of the hydrazide oxidized developer scavenger by making its oxidation more facile. Examples include carbonamido (Hammett sigma p for acetamido=0.00), aryl (−0.01), alkyl (methyl=−0.17, ethyl=−0.151), alkyloxy (methoxy =−0.27, ethoxy=−0.24), aryloxy (−0.32), amino (−0.66) and alkylamino (methylamino=−0.84, ethylamino =−0.61) groups. More preferably, the electron donating group is carbonamido, aryloxy or alkyloxy. It is further preferred that none of the $R_4$ groups be an electron withdrawing group as defined above for the $R_1$ group. It is also preferred that none of the $R_2$ groups be an electron donating group as defined above for the $R_4$ group.

The ballast group $R_3$ and the preferred electron donating group for $R_4$ may be combined into a single group by incorporating the ballasting group into the electron donating group. Examples include alkylamido, alkyl or alkyloxy groups in which the alkyl portion of the electron donating group contains at least 8, preferably at least 12, and more preferably at least 15 contiguous atoms. All of the examples for $R_3$ above are ballast groups which incorporate the preferred electron donating group.

The $R_2$, $R_3$ and $R_4$ groups may further comprise an aqueous solubilizing group as defined above for the $R_1$ group. Examples include carboxylic acids; sulfonamides; thiols; cyanamides; ureas; sulfonylureas; imides; sulfonic acids; polyethers having greater than two repeating units; amines and polyamines; cationic centers such as ammonium; sulfonium or phosphonium groups; amides such as carbonamides or phosphonamides; alcohols or polyalcohols; and salts thereof. The most preferred groups are selected from carboxy, carboxyalkyl, sulfo, sulfoalkyl, phosphato, phosphatoalkyl, phosphono, phosphonoalkyl, carbonamido, sulfonamido, hydroxy, and salts thereof. While the hydrazide scavengers of the present invention include an electron-withdrawing and aqueous-solubilizing group, $R_1$, the presence of additional aqueous-solubilizing groups may further increase the activity. The presence of an aqueous-solubilizing group within the substituents $R_2$, $R_3$ and $R_4$ is preferred.

Preferably, the objectives of the present invention are accomplished with a hydrazide scavenger represented by formula 2.

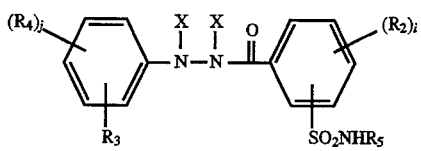

wherein $R_5$=hydrogen, acyl, alkyl or aromatic substituent

X, $R_2$, $R_3$, $R_4$, i and j are defined as above.

More preferably, the objectives of the present invention are accomplished with a hydrazide scavenger represented by formula 3.

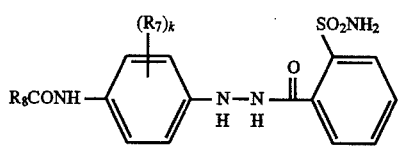

wherein $R_6$=hydrogen or acyl substituent

X, $R_3$, $R_4$, and j are defined as above.

Most preferably, the objectives of the present invention are accomplished with a hydrazide scavenger represented by formula 4.

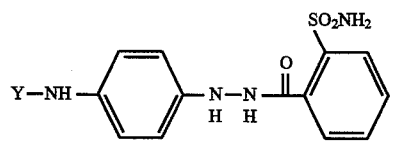

wherein $R_7$=a substituent group $R_8$=a ballasting group k=1, 2, 3 or 4

The substituent group $R_7$ may be any of the substituents described above for the $R_2$ and $R_4$ groups. It is further preferred that none of the $R_7$ groups be an electron withdrawing group as defined for the $R_1$ group. The ballasting group $R_8$ may be any of the ballasting groups defined above for the $R_3$ group.

Representative examples of the oxidized developer scavengers of the present invention are shown below, with the generic structural formula for compounds 1 to 10 below being as follows:

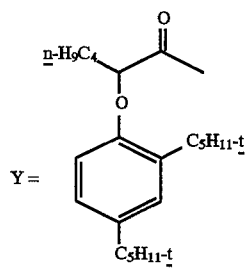

Cmpd 1:

-continued
Cmpd 2:
Y = 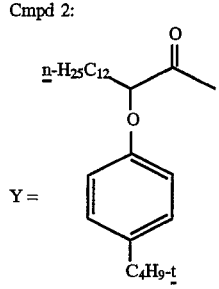
Cmpd 3:
Y = 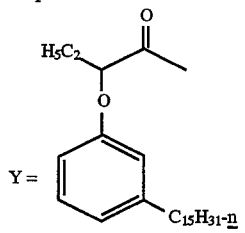
Cmpd 4:
Y = 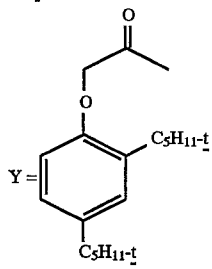
Cmpd 5:
Y = 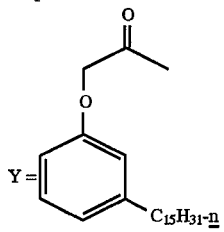
Cmpd 6:
Y = 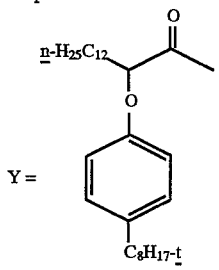
Cmpd 7:
Y = 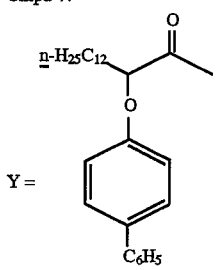

-continued
Cmpd 8:
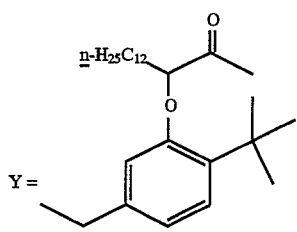
Cmpd 9:
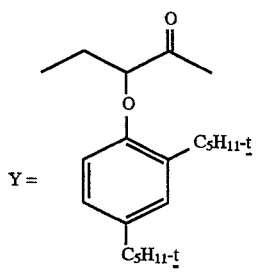
Cmpd 10:
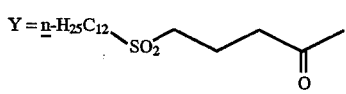
Cmpd 11:
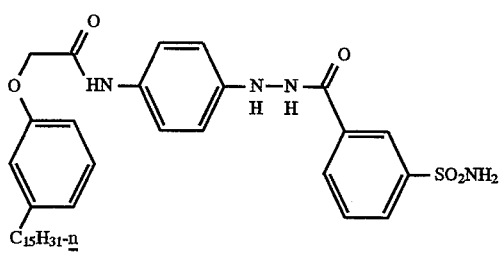
Cmpd 12:
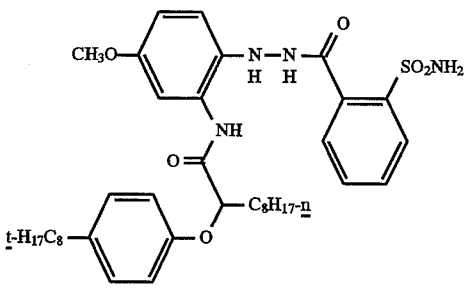
Cmpd 13:
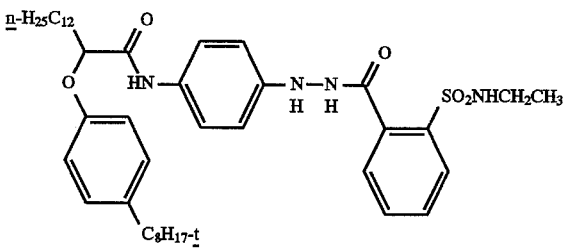

-continued
Cmpd 14:
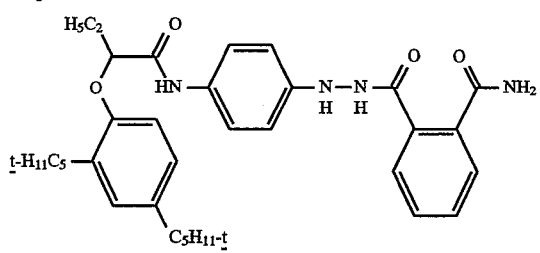
Cmpd 15:
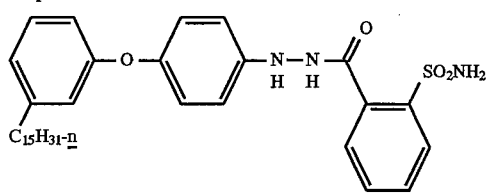
Cmpd 16:
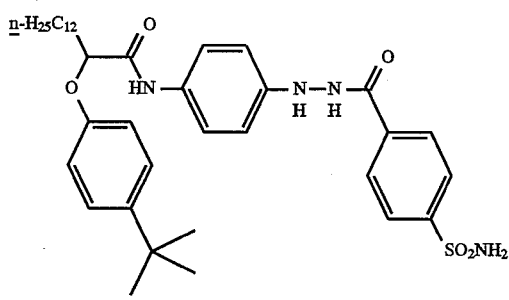
Cmpd 17:
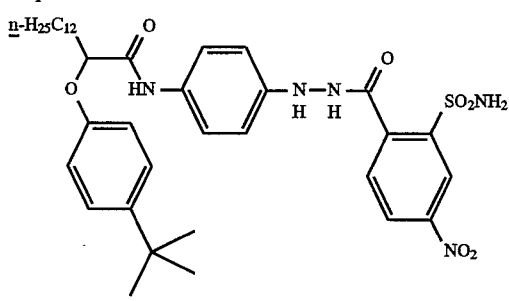
Cmpd 18:
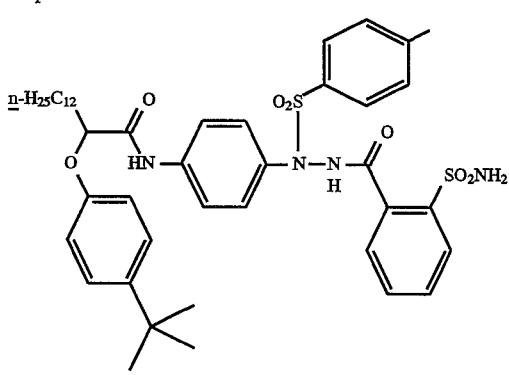

-continued
Cmpd 19:
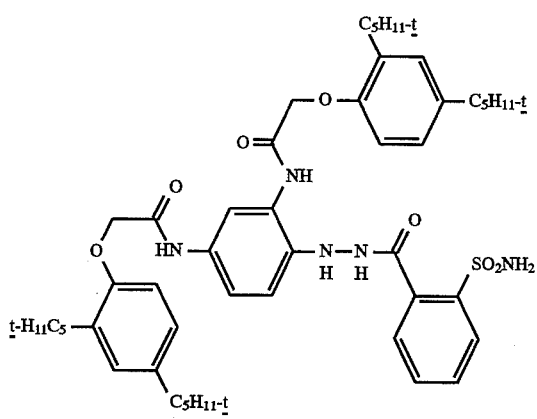
Cmpd 20:
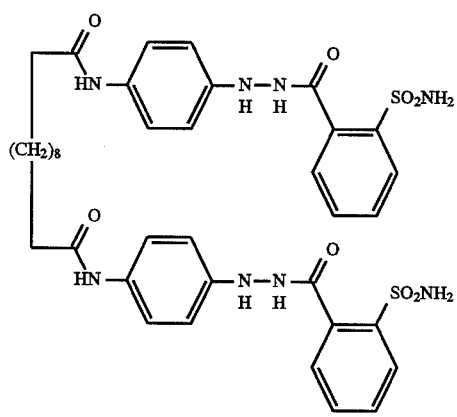
Cmpd 21:
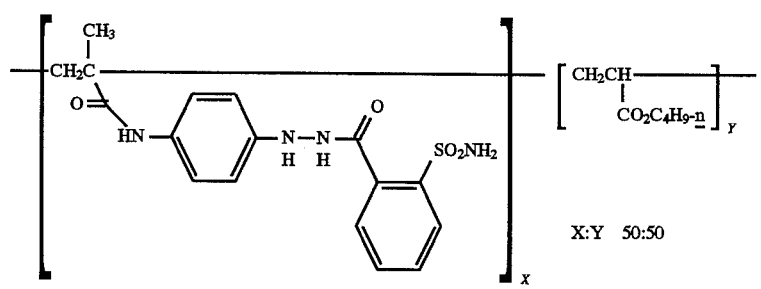
X:Y  50:50
Cmpd 22:
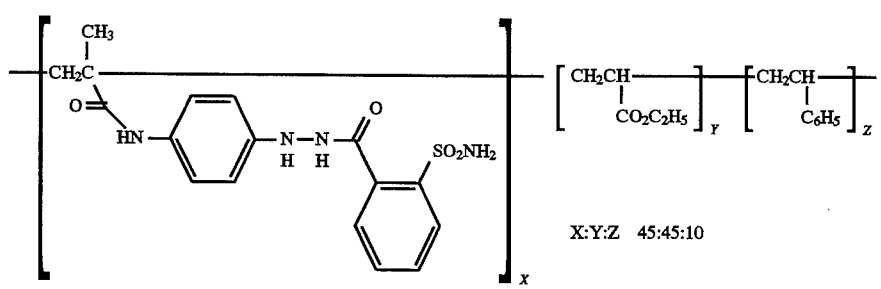
X:Y:Z  45:45:10

Cmpd 23:

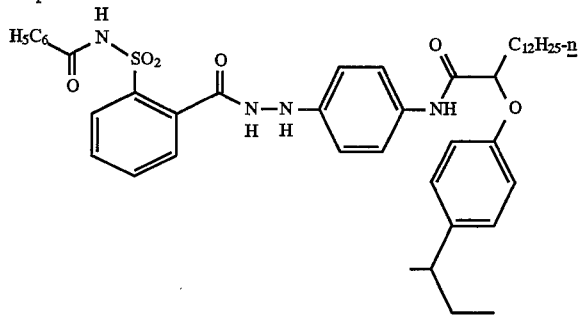

An important class of magenta-dye-image-forming couplers are the four-equivalent 5-pyrazolone couplers. Such couplers are very well known in the photographic art and are described in numerous patents such as, for example, U.S. Pat. Nos. 3,518,429, 3,907,571, 3,928,044, 3,935,015 and 4,199,361. Any of the known four-equivalent 5-pyrazolone magenta-dye-forming couplers can be advantageously utilized in association with the hydrazide scavengers of this invention.

In a preferred embodiment of the present invention, the hydrazide scavenger described herein is incorporated in a photographic element containing a 5-pyrazolone magenta-dye-forming coupler represented by either formula 5 or formula 6 as follows.

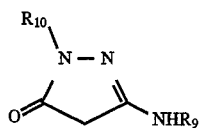

5

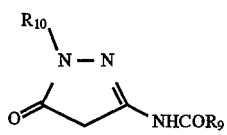

6

The $R_9$ and $R_{10}$ substituent groups are chosen independently to be a ballast group, unsubstituted or substituted alkyl, phenyl or substituted phenyl. Representative examples of these magenta couplers are shown below.

M-1:

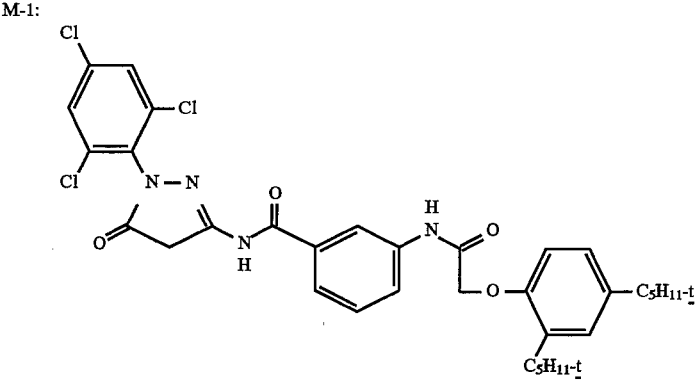

M-2:

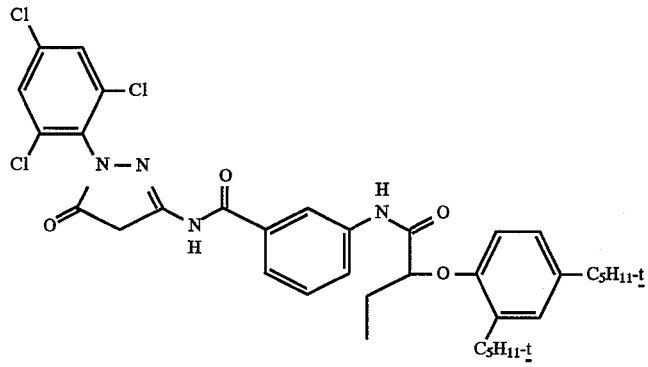

M-3:

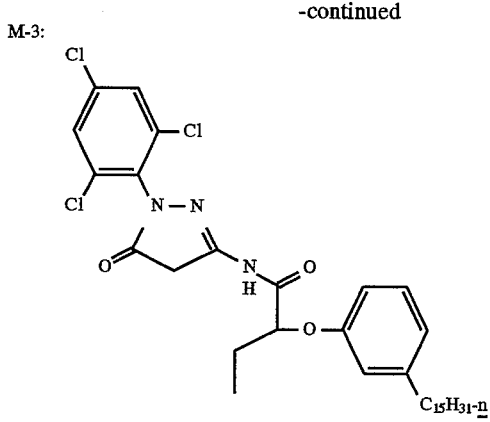

M-4:

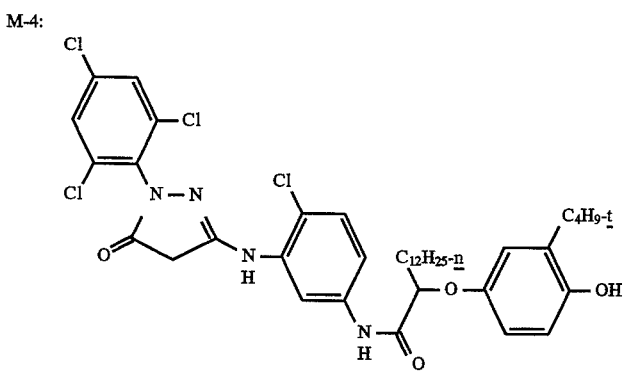

Although the hydrazide scavengers of this invention are most useful with four-equivalent 5-pyrazolone magenta couplers, they can also be used very effectively with two-equivalent 5-pyrazolone and pyrazoloazole types of magenta coupler as well. The two-equivalent 5-pyrazolone magenta-dye-forming couplers are very well known in the photographic art and are described in numerous patents such as, for example, U.S. Pat. No. 4,076,533, 4,241,168, 4,310,619, 4,840,877 and 4,914,013. Pyrazoloazole compounds are also well known as magenta-dye-forming couplers and are described in, for example, U.S. Pat. Nos. 4,443,536, 4,665,015, 4,639,413, 4,639,415, 4,559,297, 4,618,573 and 4,762,775. Some examples of particularly useful two-equivalent magenta couplers are:

M-5:

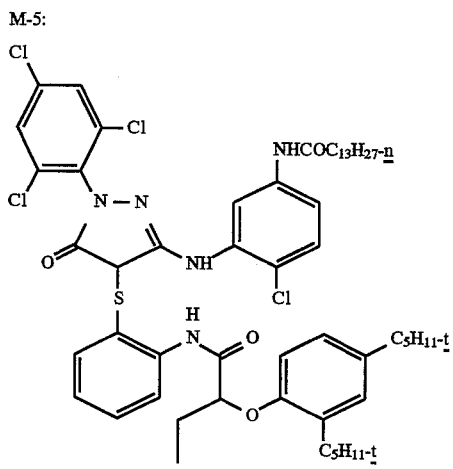

-continued

M-6:

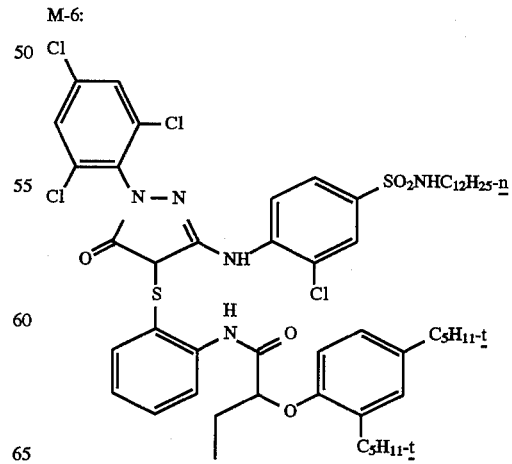

M-7:
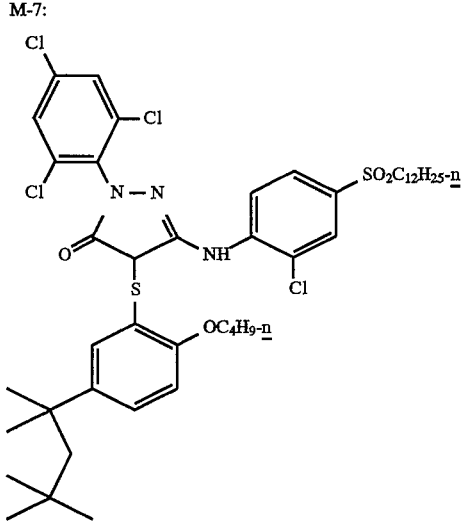

M-8:
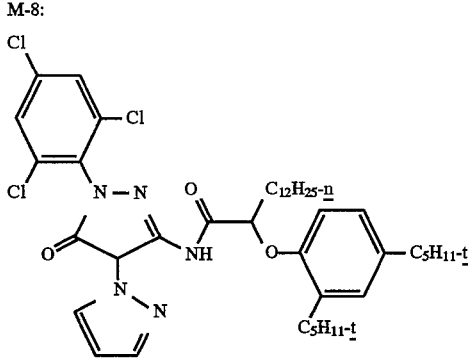

M-9:
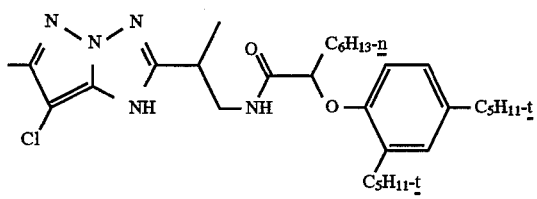

M-10:
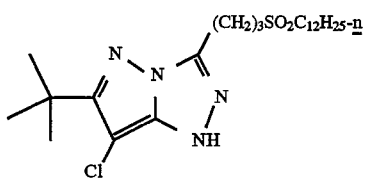

M-11:
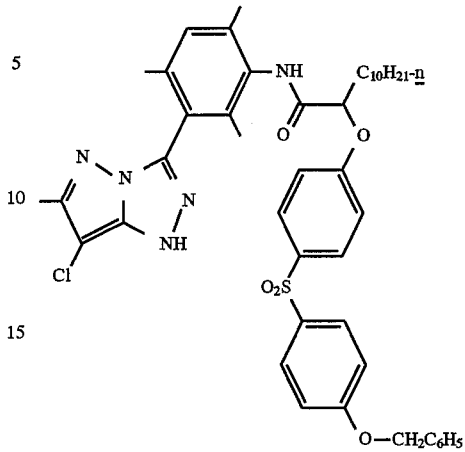

M-12:
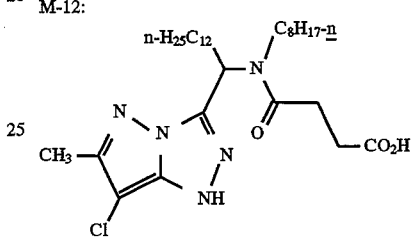

The photographic elements of the present invention can be simple black-and-white or monochrome elements comprising a support bearing a layer of silver halide emulsion or they can be multilayer and/or multicolor elements.

Color photographic elements of this invention typically contain dye image-forming units sensitive to each of the three primary regions of the spectrum. Each unit can be comprised of a single silver halide emulsion layer or of multiple emulsion layers sensitive to a given region of the spectrum. The layers of the element, including the layers of the image-forming units, can be arranged in various orders as is well known in the art.

A preferred photographic element according to this invention comprises a support bearing at least one blue-sensitive silver halide emulsion layer having associated therewith a yellow image dye-providing material, at least one green-sensitive silver halide emulsion layer having associated therewith a magenta image dye-providing material and at least one red-sensitive silver halide emulsion layer having associated therewith a cyan image dye-providing material, the element containing a hydrazide compound that functions as a scavenger in accordance with this invention. In a preferred embodiment of the invention, the scavenger is incorporated in an interlayer between silver halide emulsion layers sensitive to different regions of the visible spectrum, although it can be incorporated in an interlayer between silver halide emulsion layers sensitive to the same region of the visible spectrum. In a second preferred embodiment of the invention, the scavenger is incorporated in a silver halide emulsion layer to control curve shape. The scavenger can be incorporated in layers which also have other functions, such as, for example, antihalation layers or filter layers.

In addition to emulsion layers and interlayers, the elements of the present invention can contain auxiliary layers conventional in photographic elements, such as overcoat layers, spacer layers, filter layers, antihalation layers, pH lowering layers (sometimes referred to as acid layers and neutralizing layers), timing layers, opaque reflecting layers, opaque light-absorbing layers and the like. The support can be any suitable support used with photographic elements. Typical supports include polymeric films, paper (including polymer-coated paper), glass and the like. Details regarding supports and other layers of the photographic elements of this invention are contained in *Research Disclosure*, Item 36544, Sep., 1994.

The light-sensitive silver halide emulsions employed in the photographic elements of this invention can include coarse, regular or fine grain silver halide crystals or mixtures thereof and can be comprised of such silver halides as silver chloride, silver bromide, silver bromoiodide, silver chlorobromide, silver chloroiodide, silver chorobromoiodide, and mixtures thereof. The emulsions can be, for example, tabular grain light-sensitive silver halide emulsions. The emulsions can be negative-working or direct positive emulsions. They can form latent images predominantly on the surface of the silver halide grains or in the interior of the silver halide grains. They can be chemically and spectrally sensitized in accordance with usual practices. The emulsions typically will be gelatin emulsions although other hydrophilic colloids can be used in accordance with usual practice. Details regarding the silver halide emulsions are contained in *Research Disclosure*, Item 36544, Sep., 1994, and the references listed therein.

The photographic silver halide emulsions utilized in this invention can contain other addenda conventional in the photographic art. Useful addenda are described, for example, in *Research Disclosure*, Item 36544, September, 1994. Useful addenda include spectral sensitizing dyes, desensitizers, antifoggants, masking couplers, DIR couplers, DIR compounds, antistain agents, image dye stabilizers, absorbing materials such as filter dyes and UV absorbers, light-scattering materials, coating aids, plasticizers and lubricants, and the like.

Depending upon the dye-image-providing material employed in the photographic element, it can be incorporated in the silver halide emulsion layer or in a separate layer associated with the emulsion layer. The dye-image-providing material can be any of a number known in the art, such as dye-forming couplers, bleachable dyes, dye developers and redox dye-releasers, and the particular one employed will depend on the nature of the element, and the type of image desired.

Dye-image-providing materials employed with conventional color materials designed for processing with separate solutions are preferably dye-forming couplers; i.e., compounds which couple with oxidized developing agent to form a dye. Preferred couplers which form cyan dye images are phenols and naphthols. Preferred couplers which form magenta dye images are pyrazolones and pyrazolotriazoles. Preferred couplers which form yellow dye images are benzoylacetanilides and pivalylacetanilides.

The amount of scavenger compound employed will depend upon the particular purpose for which the scavenger is to be used and the degree of scavenging desired. Typically useful results are obtained when the scavenger is employed in an amount of between about 5 and 2000 mg/square meter.

The hydrazide compound is typically incorporated in the photographic element with the aid of a suitable solvent such as a coupler solvent. Examples of preferred coupler solvents that can be utilized for this purpose in this invention include:

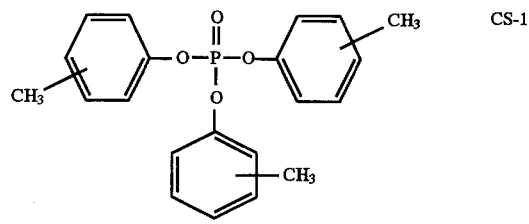

(mixture of ortho, meta and para isomers)

CS-2

CS-3

CS-4

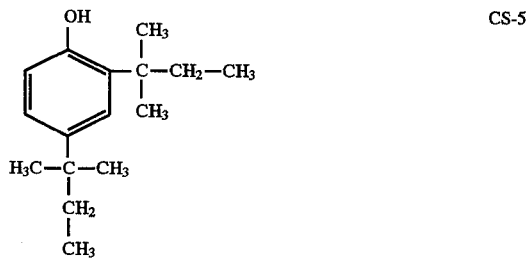

CS-5

CS-6

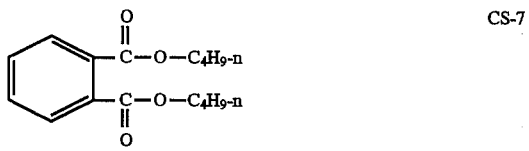

CS-7

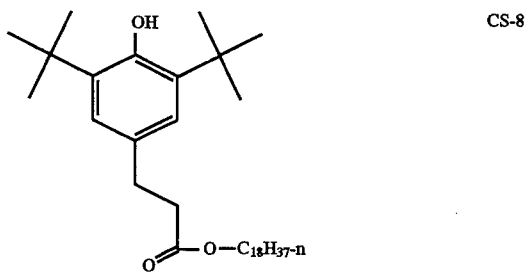

CS-8

In the practice of this invention, it is desirable to incorporate a surfactant in one or more layers of the photographic element. Examples of useful surfactants include nonionic surfactants such as SURFACTANT 10G from OLIN MATHIESON CORPORATION and anionic surfactants such as TRITON X-200E from ROHM AND HAAS COR- PORATION or AEROSOL OT from AMERICAN CYANAMID COMPANY.

The problem of sensitizing dye stain, which is minimized or avoided by the use of a scavenger in accordance with this invention, is particularly severe with photographic elements utilizing tabular grain silver halide emulsions because such emulsions typically employ very high levels of sensitizing dye. However, because of their other advantageous characteristics use of tabular grain silver halide emulsions represents a particularly important embodiment of this invention.

Specifically contemplated tabular grain emulsions for use in this invention are those in which greater than 50 percent of the total projected area of the emulsion grains is accounted for by tabular grains having a thickness of less than 0.3 micron and an average tabularity (T) of greater than 25 (preferably greater than 100), where the term "tabularity" is employed in its art recognized usage as $$T=ECD/t^2$$

where

ECD is the average equivalent circular diameter of the tabular grains in microns and t is the average thickness in microns of the tabular grains.

The average useful ECD of photographic emulsions can range up to about 10 microns, although in practice emulsion ECD's seldom exceed about 4 microns. Since both photographic speed and granularity increase with increasing ECD's, it is generally preferred to employ the smallest tabular grain ECD's compatible with achieving aim speed requirements.

Emulsion tabularity increases markedly with reductions in tabular grain thickness. It is generally preferred that aim tabular grain projected areas be satisfied by thin (t<0.2 micron) tabular grains. To achieve the lowest levels of granularity it is preferred that aim tabular grain projected areas be satisfied with ultrathin (t<0.06 micron) tabular grains. Tabular grain thicknesses typically range down to about 0.02 micron. However, still lower tabular grain thicknesses are contemplated. For example, Daubendiek et al U.S. Pat. No. 4,672,027 reports a 3 mole percent iodide tabular grain silver bromoiodide emulsion having a grain thickness of 0,017 micron.

As noted above, tabular grains of less than the specified thickness account for at least 50 percent of the total grain projected area of the emulsion. To maximize the advantages of high tabularity it is generally preferred that tabular grains satisfying the stated thickness criterion account for the highest conveniently attainable percentage of the total grain projected area of the emulsion. For example, in preferred emulsions, tabular grains satisfying the stated thickness criteria above account for at least 70 percent of the total grain projected area. In the highest performance tabular grain emulsions, tabular grains satisfying the thickness criteria above account for at least 90 percent of total grain projected area.

In a particularly preferred embodiment, the present invention provides a multicolor photographic element capable of forming a dye image, which element comprises a support having thereon:

a blue-recording yellow-dye-image forming layer unit, a green-recording magenta-dye-image-forming layer unit, and a red-recording cyan-dye-image-forming layer unit, each of the dye-image-forming layer units comprising at least one silver halide emulsion layer containing at least one sensitizing dye; the element comprising at least one interlayer positioned between dye-image-forming layer units sensitive to different regions of the visible spectrum and at least one interlayer or silver halide emulsion layer containing a hydrazide compound as hereinabove described.

The photographic elements of this invention can be exposed to actinic radiation, typically in the visible region of the spectrum, to form a latent image and can then be processed to form a visible dye image. Processing to form a visible dye image includes the step of contacting the element with a color developing agent to reduce developable silver halide and oxidize the color developing agent. Oxidized color developing agent in turn reacts with the coupler to yield a dye.

Preferred color developing agents are p-phenylenediamines such as: 4-amino-N,N-diethylaniline hydrochloride, 4-amino-3-methyl-N,N-diethylaniline hydrochloride, 4-amino-3-methyl-N-ethyl-N-(b-(methanesulfonamido) ethyl)aniline sesquisulfate hydrate, 4-amino-3-methyl-N-ethyl-N-(b-hydroxyethyl)aniline sulfate, 4-amino-3-b-(methanesulfonamido)ethyl-N,N-diethylaniline hydrochloride and 4-amino-N-ethyl-N-(2-methoxyethyl)-m-toluidine di-p-toluene sulfonic acid.

Development is usually followed by the conventional steps of bleaching, fixing, or bleach-fixing, to remove silver or silver halide, washing, and drying.

The following example illustrates the synthesis of a hydrazide oxidized developer scavenger useful in the present invention. The synthesis scheme described, Scheme II, is representative and can be varied by those skilled in the art to obtain other useful hydrazide oxidized developer scavengers.

Scheme II

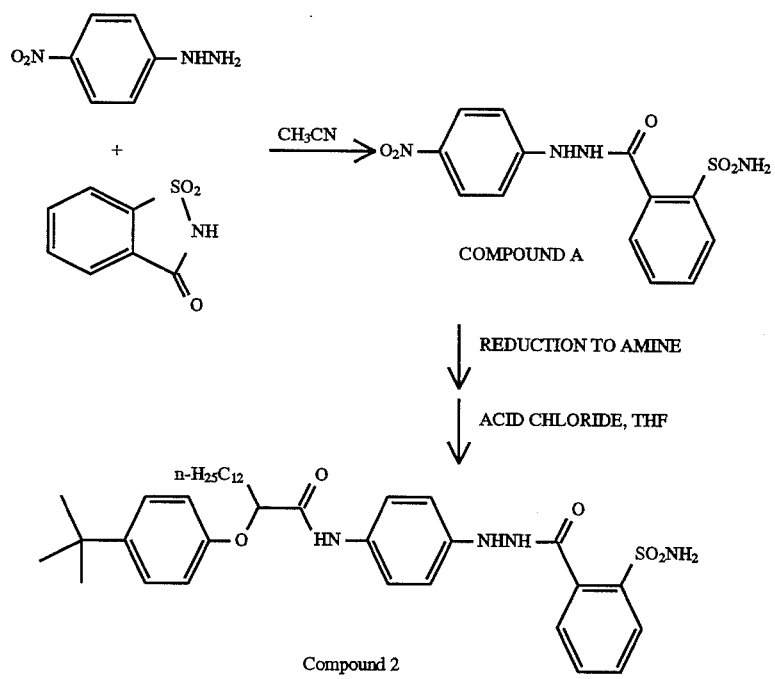

Preparation of Compound A

Saccharin (18.3 g, 0.1 mole) and p-nitrophenylhydrazine (15 g, 0.1 mole) were mixed in acetonitrile (100 mL) and heated at reflux for 4 hours. A solid formed; the reaction was cooled to room temperature and filtered. The solid was collected and washed with acetonitrile to yield Compound A (24 g, 71% yield). The NMR spectrum was consistent with the desired product.

Preparation of Compound 2

Compound A (14 g, 45 mmol) was mixed with 10% palladium on carbon catalyst (1 g) and tetrahydrofuran. The mixture was shaken with hydrogen gas (58 psi) on a Parr shaker for 24 hours at room temperature. The reaction was aspirated to remove excess hydrogen and a tetrahydrofuran solution of ballast acid chloride imidazole adduct [prepared from the acid chloride (15.1 g, 40 mmole) and imidazole (5.4 g, 80 mmol) stirred in tetrahydrofuran at room temperature for 2 hours and filtered] was added dropwise at room temperature under nitrogen. The reaction was stirred for 2 hours, filtered through super cel and concentrated. The residue was taken up in ethyl acetate (200 mL) and washed twice with 10% aqueous hydrochloric acid. The organic layer was dried (MgSO$_4$) and concentrated. The residue was chromatographed using 20% ethyl acetate in dichloromethane to yield Compound 2 (22 g, 83% yield). The NMR spectrum was consistent with the desired product.

The practice of the invention is described in detail below with reference to specific illustrative examples, but the invention is not to be construed as being limited thereto. The ingredients employed in the working examples which have not already been identified hereinabove are described below.

SCV-1:

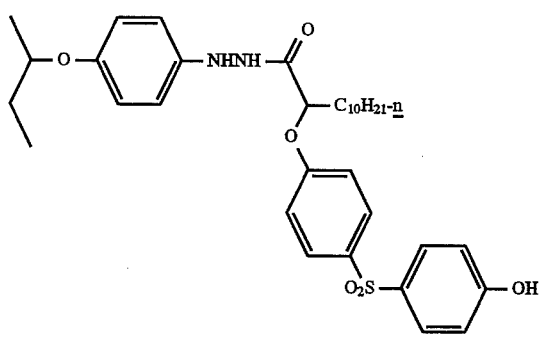

-continued
SCV-2:
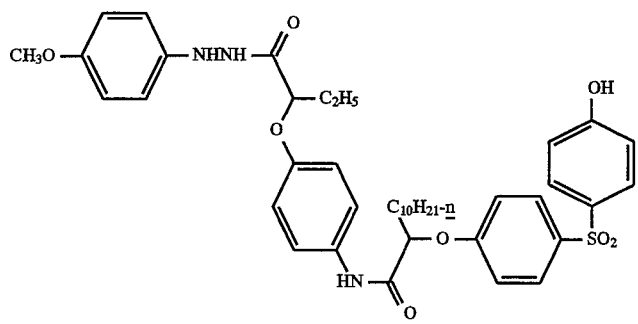
SCV-3:
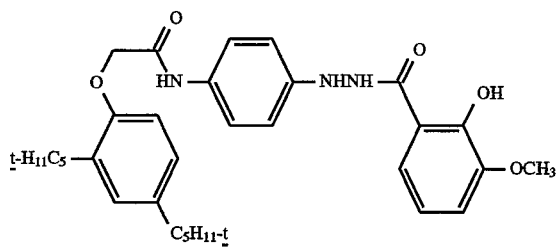
SCV-4:
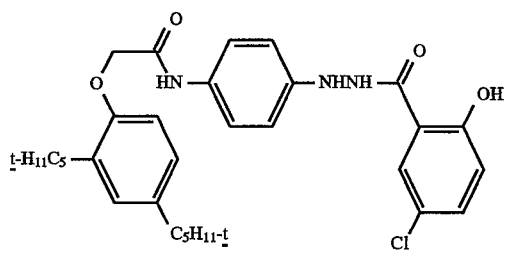
SCV-5:
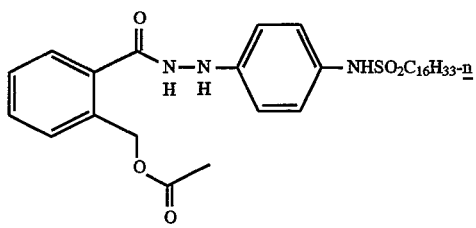
SCV-6:
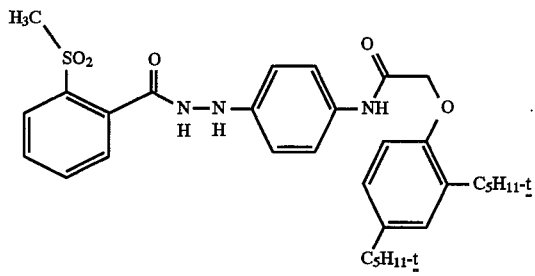

C-1: 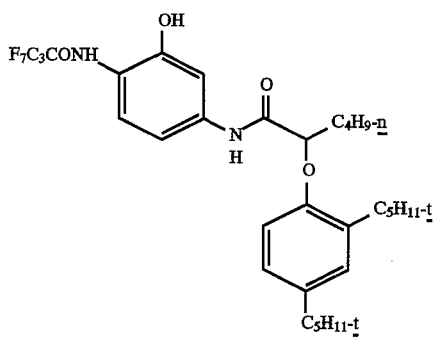
YEL-1: 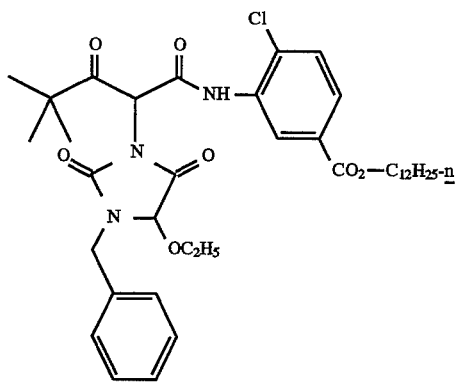
YEL-2: 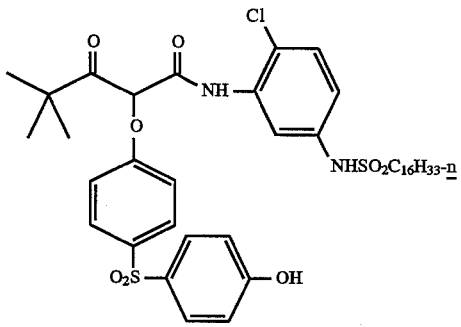
FD-1: 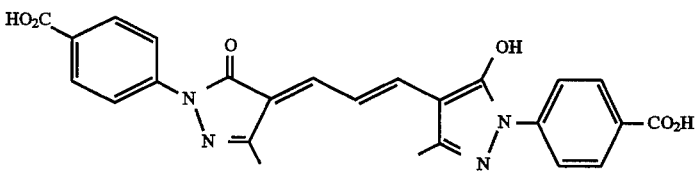
FD-2: 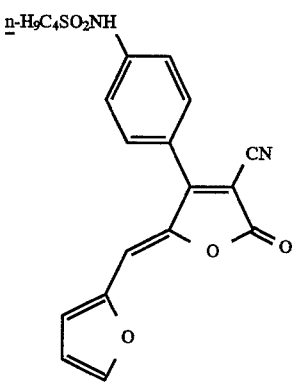

-continued
SD-1:
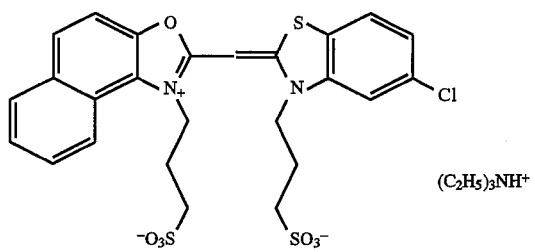
(C₂H₅)₃NH⁺
SD-2:
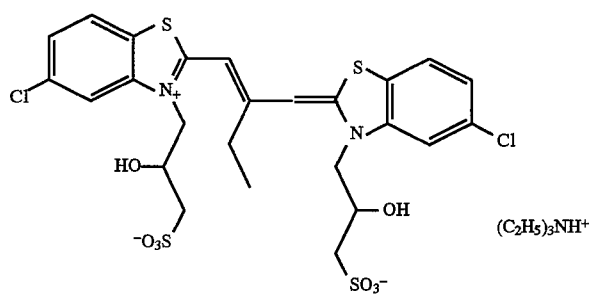
(C₂H₅)₃NH⁺
SD-3:
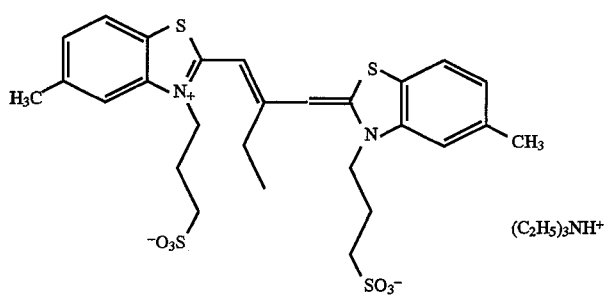
(C₂H₅)₃NH⁺
SD-4:
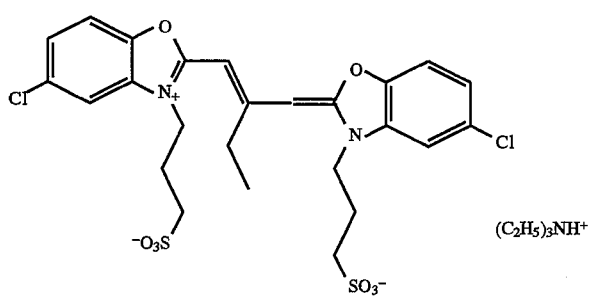
(C₂H₅)₃NH⁺
SD-5:
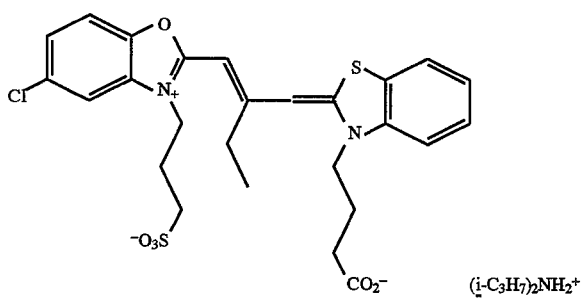
(i-C₃H₇)₂NH₂⁺

-continued
SD-6:
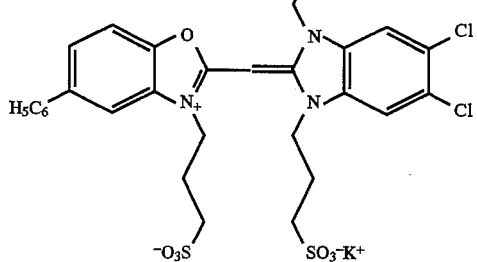
SD-7:
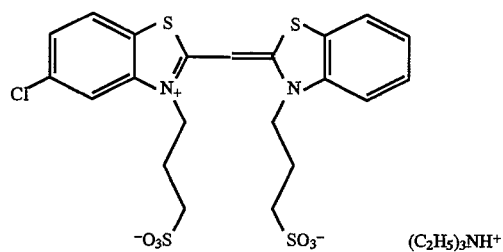
SD-8:
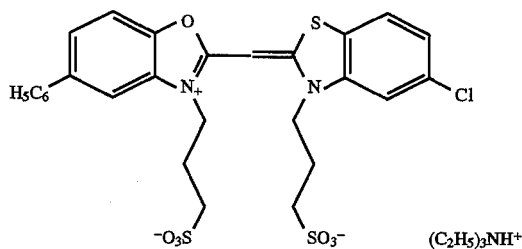
SD-9:
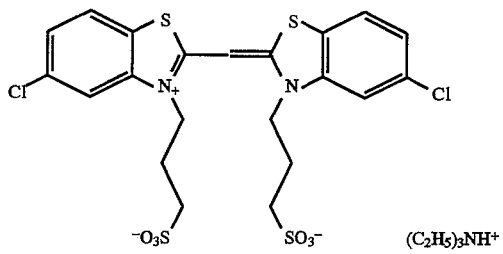
SD-10:
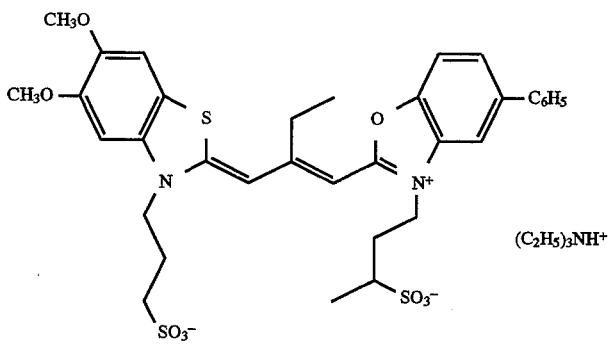
UV-1:
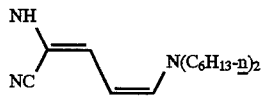

UV-2:

[Structure: 2-(2H-benzotriazol-2-yl)-4,6-di-tert-pentylphenol]

UV-3:

[Structure: 2-(5-chloro-2H-benzotriazol-2-yl)-6-tert-butyl-4-iodophenol]

I-1:

[Structure: HO₂C-CH₂-C(=CH-S)-N=C-SH]

L-1:

$$\left[\begin{array}{c}CH_3\\|\\-CH_2C-\\|\\CO_2C_4H_9\text{-}\underline{n}\end{array}\right]_{85} \left[\begin{array}{c}-CH_2CH-\\|\\C=O\\|\\NH\\|\\CH_3-C-CH_3\\|\\CH_2SO_3H\end{array}\right]_{10} \left[\begin{array}{c}CH_3\\|\\-CH_2C-\\|\\C=O\\|\\OCH_2CH_2\\|\\O\\|\\C=O\\|\\CH_2\\|\\C=O\\|\\CH_3\end{array}\right]_{5}$$

Hardener H-1

1,1-[methylenebis(sulfonyl)]bis-ethene

Hardener H-2

1,1-[oxybis(methylenesulfonyl)]bis-ethene

Solvent S-1

1,4-Cyclohexylenedimethylene bis(2-ethylhexanoate)

Solvent S-2

Oleyl alcohol

EXAMPLE 1

On a cellulose triacetate film support provided with a subbing layer was coated each layer having the composition set forth below to prepare a single layer color photographic light-sensitive material which was designated sample 101. In the composition of the layers, the coating amounts are shown as g/m².

| First Layer: Antihalation Layer | |
|---|---|
| Black Colloidal Silver | 0.43 (as silver) |
| UV Dye UV-1 | 0.04 |
| Dispersed in Solvent S-1 | 0.04 |
| Gelatin | 2.44 |
| Second Layer: Intermediate Layer | |
| Gelatin | 1.22 |
| Third Layer: Light Sensitive Layer | |
| Silver iodobromide Emulsion 1.74 × 0.1 micron tabular emulsion 3% bulk iodide spectrally sensitized with dye SD-1 | 1.08 (as silver) |
| Cyan Coupler C-1 | 1.61 |
| Dispersed in Solvent CS-7 | 0.81 |
| Gelatin | 2.15 |
| Fourth Layer: Overcoat Layer | |
| Gelatin | 2.15 |
| Hardener H-1 | 0.14 |

Samples 102 to 105 were prepared in the same manner as described above for Sample 101 except for the addition of the oxidized developer scavenger listed in Table I to the Third Layer. The added Dox scavengers were coated at the levels (in g/m$^2$) shown in Table I; these levels result in all of the Dox scavengers being coated at equimolar levels (0.38 mmol/m$^2$).

Each of the samples thus prepared was cut into a 35 mm width strip. The samples were exposed to a step exposure using white light. The samples were then processed using standard Kodak E-6 processing solutions and methods except that the first developer processing time was reduced from the standard 6 minutes to 4 minutes to compensate for the rapid development rate of a single layer photographic material. The Status A blue density was measured for the Dmin of each sample and is reported in Table I.

TABLE I

| Sample | Dox Scavenger | Level | Blue Dmin |
| --- | --- | --- | --- |
| 101 | None (Check) | — | 0.07 |
| 102 | SCV-3 (Comparison) | 0.20 | 0.11 |
| 103 | SCV-4 (Comparison) | 0.20 | 0.10 |
| 104 | Cmpd 1 (Invention) | 0.24 | 0.07 |
| 105 | Cmpd 2 (Invention) | 0.25 | 0.07 |

From the results shown in Table I it is clear that, compared to the no scavenger check, the samples using the oxidized developer scavengers of the present invention exhibit no increase in blue Dmin. The comparison Dox scavengers, which do not incorporate the electron withdrawing and aqueous solubilizing group of the present invention on the aromatic ring linked to the carbonyl of the hydrazide, exhibit an increased blue Dmin.

EXAMPLE 2

On a cellulose triacetate support provided with a subbing layer was coated each layer having the composition set forth below to prepare a single layer color photographic light-sensitive material which was designated sample 201. In the composition of the layers, the coating amounts are shown as g/m$^2$.

| First Layer: Antihalation Layer | |
| --- | --- |
| Black Colloidal Silver | 0.43 (as silver) |
| UV Dye UV-1 | 0.04 |
| Dispersed in Solvent S-1 | 0.04 |
| Gelatin | 2.44 |
| Second Layer: Intermediate Layer | |
| Gelatin | 1.22 |
| Third Layer: Light Sensitive Layer | |
| Silver Iodobromide Emulsion 1.74 × 0.1 micron tabular emulsion 3% bulk iodide spectrally sensitized with dye SD-1 | 1.08 (as silver) |
| Magenta Coupler M-1 | 1.61 |
| Dispersed in Solvent CS-1 | 0.81 |
| Gelatin | 2.15 |
| Fourth Layer: Overcoat Layer | |
| Gelatin | 2.15 |
| Hardener H-1 | 0.14 |

Samples 202 to 206 were prepared in the same manner as described above for Sample 201 except for the addition of the oxidized developer scavenger listed in Table II to the Third Layer. The added Dox scavengers were coated at the levels (in g/m$^2$) shown in Table II; these levels result in all of the Dox scavengers being coated at equimolar levels (0.38 mmol/m2).

Each of the samples thus prepared was cut into a 35mm width strip. The samples were exposed to a step exposure using white light. The samples were then processed using standard Kodak E-6 processing solutions and methods except that the first developer processing time was reduced from the standard 6 minutes to 4 minutes to compensate for the rapid development rate of a single layer photographic material. The Status A green density was then measured for all of the steps. A spectrophotometric analysis was then performed on the step closest to 1.0 density and the data was normalized to 1.0 density at 550 nm which is the Lambda (Max.) for magenta coupler M-1. The unwanted blue density at 430 nm is reported in Table II.

TABLE II

| Sample | Dox Scavenger | Level | Density | Delta Density |
| --- | --- | --- | --- | --- |
| 201 | None (Check) | — | 0.24 | — |
| 202 | SCV-1 (Comparison) | 0.24 | 0.36 | 0.12 |
| 203 | SCV-2 (Comparison) | 0.28 | 0.39 | 0.15 |
| 204 | Cmpd 1 (Invention) | 0.24 | 0.31 | 0.07 |
| 205 | Cmpd 2 (Invention) | 0.25 | 0.32 | 0.08 |
| 206 | Cmpd 3 (Invention) | 0.26 | 0.31 | 0.07 |

From the results shown in Table II it is clear that the samples using the oxidized developer scavengers of the present invention have significantly less unwanted blue density than the comparison Dox scavengers, which do not incorporate the ballast group of the present invention on the aromatic ring linked to the nitrogen of the hydrazide.

EXAMPLE 3

On a cellulose triacetate support provided with a subbing layer was coated each layer having the composition set forth below to prepare a multilayer color photographic light-sensitive material which was designated sample 301. In the composition of the layers, the coating amounts are shown as g/m$^2$.

| First Layer: Antihalation Layer | |
| --- | --- |
| Black Colloidal Silver | 0.43 (as silver) |
| UV Dye UV-1 | 0.04 |
| Dispersed in Solvent S-1 | 0.04 |
| Gelatin | 2.44 |
| Second Layer: Intermediate Layer | |
| Gelatin | 1.22 |
| Third Layer: Slow Red Sensitive Layer | |
| Silver Iodobromide Emulsion tabular emulsion (13:1 aspect ratio) 3% bulk iodide spectrally sensitized with dyes SD-2 and SD-3 | 0.25 (as silver) |
| Silver Iodobromide Emulsion tabular emulsion (6:1 aspect ratio) 4% bulk iodide spectrally sensitized with dyes SD-2 and SD-3 | 0.20 (as silver) |
| Silver Iodobromide Emulsion 0.15 µ equivalent spherical diameter 4.8% bulk iodide spectrally sensitized | 0.12 (as silver) |
| Fine Grain Silver Bromide 0.07 µ equivalent spherical diameter | 0.05 |
| Cyan Coupler C-1 | 0.23 |
| Dispersed in Solvent CS-7 | 0.11 |
| Gelatin | 0.86 |
| Fourth Layer: Fast Red Sensitive Layer | |
| Silver Iodobromide Emulsion tabular emulsion (12:1 aspect ratio) 1.5% bulk iodide spectrally sensitized with dyes SD-2 and SD-3 | 0.68 (as silver) |
| Silver Iodobromide Emulsion 0.15 µ equivalent spherical diameter 4.8% bulk iodide spectrally sensitized | 0.12 (as silver) |

| | |
|---|---|
| Fine Grain Silver Bromide 0.07 μ equivalent spherical diameter | 0.08 |
| Cyan Coupler C-1 | 1.36 |
| Dispersed in Solvent CS-7 | 0.68 |
| Gelatin | 2.15 |
| Fifth Layer: Interlayer | |
| Filter Dye FD-1 | 0.06 |
| Inhibitor I-1 | 0.001 |
| Gelatin | 0.61 |
| Sixth Layer: Slow Green Sensitive Layer | |
| Silver Iodobromide Emulsion tabular emulsion (7:1 aspect ratio) 3% bulk iodide spectrally sensitized with dyes SD-4 and SD-5 | 0.27 (as silver) |
| Silver Iodobromide Emulsion tabular emulsion (6:1 aspect ratio) 4% bulk iodide spectrally sensitized with dyes SD-4 and SD-5 | 0.22 (as silver) |
| Silver Iodobromide Emulsion 0.15 μ equivalent spherical diameter 4.8% bulk iodide spectrally sensitized | 0.11 (as silver) |
| Magenta Coupler M-1 | 0.05 |
| Magenta Coupler M-2 | 0.11 |
| Co-dispersed in Solvent CS-1 | 0.08 |
| Gelatin | 0.86 |
| Seventh Layer: Fast Green Sensitive Layer | |
| Silver Iodobromide Emulsion tabular emulsion (11:1 aspect ratio) 2% bulk iodide spectrally sensitized with dyes SD-4 and SD-5 | 0.62 (as silver) |
| Silver Iodobromide Emulsion 0.15 μ equivalent spherical diameter 4.8% bulk iodide spectrally sensitized | 0.06 (as silver) |
| Magenta Coupler M-1 | 0.34 |
| Magenta Coupler M-2 | 0.78 |
| Co-dispersed in Solvent CS-1 | 0.56 |
| Gelatin | 1.94 |
| Eighth Layer: Interlayer | |
| Filter Dye FD-2 | 0.22 |
| Gelatin | 0.61 |
| Ninth Layer: Slow Blue Sensitive Layer | |
| Silver Iodobromide Emulsion tabular emulsion (13:1 aspect ratio) 2% bulk iodide spectrally sensitized with dyes SD-6 and SD-7 | 0.48 (as silver) |
| Yellow Coupler YEL-1 | 0.48 |
| Dispersed in Solvent CS-7 | 0.16 |
| Gelatin | 0.86 |
| Tenth Layer: Fast Blue Sensitive Layer | |
| Silver Iodobromide Emulsion tabular emulsion (22:1 aspect ratio) 3% bulk iodide spectrally sensitized with dyes SD-8 and SD-9 | 0.65 (as silver) |
| Yellow Coupler YEL-1 | 1.66 |
| Dispersed in Solvent CS-7 | 0.56 |
| Gelatin | 2.37 |
| Eleventh Layer: First Protective Layer | |
| UV Dye UV-2 | 0.38 |
| UV Dye UV-3 | 0.07 |
| UV Dye UV-1 | 0.13 |
| Dispersed in Latex L-1 | 0.65 |
| Gelatin | 1.40 |
| Twelfth Layer: Second Protective Layer | |
| Fine Grain Silver Bromide 0.07 μ equivalent spherical diameter | 0.12 (as silver) |
| Matte 3.3 μ spherical diameter | 0.02 |
| Hardener H-1 | 0.29 |
| Gelatin | 0.98 |

Sample 302 was prepared in the same manner as described above for Sample 301 except that 0.11 g/m² of Comparative Dox Scavenger SCV-1 was added to both the Fifth and Eighth layers. Sample 303 was prepared in the same manner as described above for Sample 301 except that 0.11 g/m² of Invention Cmpd 2 was added to both the Fifth and Eighth Layers.

Each of the samples thus prepared was cut into a 35 mm width strip. The samples were exposed to create a series of 21 magenta density steps by flashing out the blue and red sensitive layers (using a KODAK WRATTEN 29 and WRATTEN 98 filter, respectively) and exposing the green-sensitive layers using a step tablet and a KODAK WRATTEN 99 filter. The samples were then processed using standard Kodak E-6 processing solutions and methods. The Status A red, green, and blue densities were measured and converted to equivalent neutral densities using standard procedures. The variation of blue density as a function of green density was then evaluated for the samples to determine the effect of the variations on the hue of the magenta density steps. This data is tabulated in Table III.

TABLE III

| | | Blue Density @ Green Density of | | |
|---|---|---|---|---|
| Sample | Dox Scavenger | 0.50 | 1.00 | 1.50 |
| 301 | None (Check) | 0.163 | 0.175 | 0.205 |
| 302 | SCV-1 (Comparison) | 0.170 | 0.180 | 0.200 |
| 303 | Cmpd 2 (Invention) | 0.155 | 0.160 | 0.175 |

Compared to Sample 301 the comparison Sample 302 has greater blue contamination of the magenta dye except at a density of 1.5 where wandering of oxidized developer to the yellow layer is greater in Sample 301 due to the absence of an interlayer scavenger. Compared to both Samples 301 and 302 the invention Sample 303 has less blue contamination of the magenta dye at all densities due to both efficient scavenging of oxidized developer (in comparison to Sample 301) and due to the formation of less yellow stain (in comparison to Sample 302).

EXAMPLE 4

On a cellulose acetate-butyrate support provided with a subbing layer was coated each layer having the composition set forth below to prepare a multilayer color photographic light-sensitive material which was designated sample 400. In the composition of the layers, the coating amounts are shown as g/m².

| | |
|---|---|
| First Layer: Antihalation Layer | |
| Black Colloidal Silver | 0.32 (as silver) |
| Gelatin | 4.89 |
| Second Layer: Light Sensitive Layer | |
| Silver Iodobromide Emulsion spectrally sensitized with dyes SD-2 and SD-10 | 2.42 (as silver) |
| Yellow Coupler YEL-2 | 1.08 |
| Gelatin | 2.15 |
| Third Layer: Interlayer | |
| Gelatin | 0.65 |
| Fourth Layer: Receiving Layer | |
| Magenta Coupler M-12 | 0.33 |
| Dispersed in Solvents CS-5 and S-2 | 0.16 0.16 |
| Gelatin | 2.69 |
| Fifth Layer: Overcoat Layer | |
| Hardener H-2 | 0.28 |
| Gelatin | 5.38 |

Samples 401 to 414 were prepared in the same manner as described above for Sample 400 except for the addition of 0.007 mole/m² of the oxidized developer scavenger listed in Table IV to the Third layer. The added Dox scavengers were dispersed in N,N-dibutyllauramide at a 1:0.5 ratio of scavenger:solvent.

Each of the samples thus prepared was cut into a 35mm width strip. The samples were exposed imagewise through a stepped density test object and were subjected to the KODAK FLEXICOLOR (C41) Process as described in British Journal of photography Annual, 1988, pp. 196–198. The Status M green density was measured using standard procedures. In this format, magenta dye can be formed only by the wandering of oxidized developer from the layer in which it is generated (Second layer) through the interlayer to the layer containing magenta coupler (Fourth layer). Thus, the ability of the Dox scavenger to prevent oxidized developer from wandering can be evaluated by the difference in green density measured at minimum and maximum exposure as compared to the check, Sample 400, which contains no scavenger in the interlayer.

Delta Density=Test Sample (Green Dmax–Green Dmin)–Sample 400 (Green Dmax–Green Dmin)

This data is tabulated in Table IV. More negative delta green density values indicate improved scavenging.

TABLE IV

| Sample | Dox Scavenger | Delta Density |
| --- | --- | --- |
| 401 | SCV-1 (Comparison) | −0.127 |
| 402 | SCV-5 (Comparison) | −0.078 |
| 403 | SCV-6 (Comparison) | −0.085 |
| 404 | Cmpd 1 (Invention) | −0.119 |
| 405 | Cmpd 2 (Invention) | −0.151 |
| 406 | Cmpd 3 (Invention) | −0.145 |
| 407 | Cmpd 4 (Invention) | −0.180 |
| 408 | Cmpd 5 (Invention) | −0.134 |
| 409 | Cmpd 6 (Invention) | −0.122 |
| 410 | Cmpd 7 (Invention) | −0.185 |
| 411 | Cmpd 8 (Invention) | −0.146 |
| 412 | Cmpd 9 (Invention) | −0.139 |
| 413 | Cmpd 11 (Invention) | −0.185 |
| 414 | Cmpd 23 (Invention) | −0.138 |

In Table IV comparison samples 401 to 403 use typical hydrazide scavengers that do not fall within the structures of the present invention. Note that while SCV-1 has good activity in a color negative format, as demonstrated in Examples 2 and 3 above, it has unacceptable yellow stain in a reversal format. Also note that both SCV-5 and SCV-6 have poor activity in a color negative format. These hydrazide Dox scavengers lack the electron withdrawing and aqueous solubilizing group of the present invention. In particular, the comparison of samples 403 and 407 (SCV-6 and Cmpd 4) illustrates that the presence of an electron withdrawing group alone (Hammet sigma p for methyl sulfonyl=0.68) results in poor Dox scavenging activity while the presence of an electron withdrawing and solubilizing group results in good Dox scavenging activity. The hydrazide Dox scavengers of the present invention have good activity in a color negative format. In particular, the comparison between samples 408 and 413 (Cmpd 5, ortho-aminosulfonyl, and Cmpd 11, meta-aminosulfonyl) demonstrates that, while preferred to maximize electronic effects and the potential for anchimeric assistance, the electron withdrawing and aqueous solubilizing group does not have to be in the ortho position for good activity.

The invention has been described in detail, with particular reference to certain preferred embodiments thereof, but it should be understood that variations and modifications can be effected within the spirit and scope of the invention.

We claim:

1. A photographic element comprising a support bearing at least one silver halide emulsion layer having associated therewith a hydrazide compound that functions as a scavenger for oxidized developing agent; said hydrazide compound having the formula:

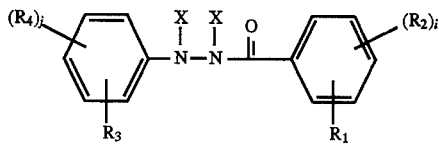

wherein each X is, independently, a hydrogen atom or a process-cleavable group;

$R_1$ is an electron-withdrawing and aqueous-solubilizing group;

each $R_2$ is, independently, a hydrogen atom or a monovalent organic substituent;

$R_3$ is a ballasting group;

each $R_4$ is, independently, a hydrogen atom or a monovalent organic substituent;

i is an integer with a value of 1 to 4; and j is an integer with a value of 1 to 4.

2. A photographic element as claimed in claim 1, wherein each X represents a hydrogen atom.

3. A photographic element as claimed in claim 1, wherein at least one X represents a $C_1$–$C_{30}$ alkylsulfonyl group, a $C_6$–$C_{30}$ arylsulfonyl group or a $C_1$–$C_{30}$ acyl group.

4. A photographic element as claimed in claim 1, wherein at least one X represents a phenylsulfonyl group or substituted phenylsulfonyl group in which the sum of the Hammett substituent constants is at least −0.5; a benzoyl group or substituted benzoyl group in which the sum of the Hammett substituent constants is at least −0.5; or a linear chain, branched or cyclic unsubsituted aliphatic acyl group or substituted aliphatic acyl group having halogen, ether, sulfonamido, carbonamido, hydroxyl, carboxyl, or sulfonic acid substituent groups.

5. A photographic element as claimed in claim 1, wherein $R_1$ is a group having both (1) a Hammett sigma p value greater than −0.10 and (2) intrinsic hydrophilicity or the capability of substantial ionization under processing conditions.

6. A photographic element as claimed in claim 1, wherein $R_1$ is an aminosulfonyl group.

7. A photographic element as claimed in claim 1, wherein $R_1$ is an aminocarbonyl group.

8. A photographic element as claimed in claim 1, wherein the $R_1$ group is in the ortho position to the carbonyl of said hydrazide.

9. A photographic element as claimed in claim 1, wherein $R_3$ is a group containing at least 12 contiguous atoms and including substituted or unsubstituted alkyl, aryl or aralkyl groups.

10. A photographic element as claimed in claim 1, wherein $R_3$ is a group represented by one of the following formulae:

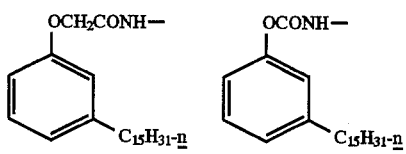

-continued

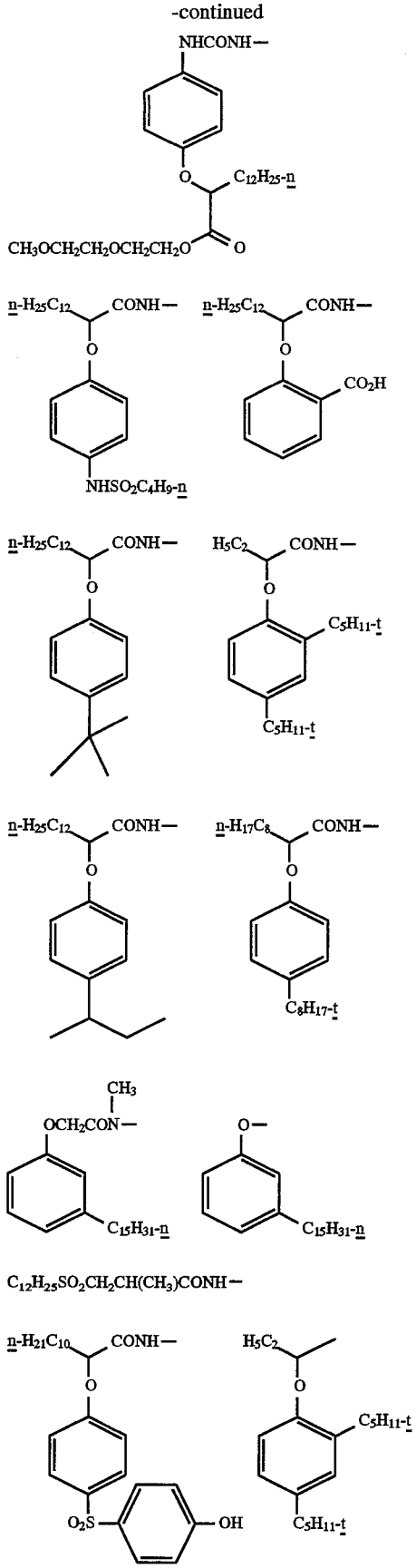

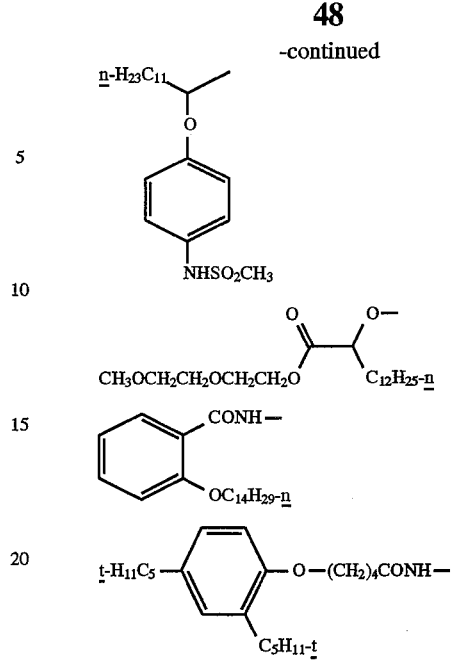

11. A photographic element as claimed in claim 1, wherein $R_2$ and $R_4$ are, independently, alkyl, cycloalkyl, alkenyl, cycloalkenyl, alkynyl, aryl, heteroaryl, heterocyclyl, alkoxy, heterocyclyloxy, aryloxy, siloxy, alkylthio, arylthio, heterocyclylthio, hydroxy, halogen, cyano, nitro, alkoxycarbonyl, alkoxycarbonylamino, aryloxycarbonyl, aryloxycarbonylamino, aminocarbonyl, carboxy, acyl, acyloxy, amino, alkylamino, anilino, imido, ureido, carbonamido, carbamoyl, carbamoyloxy, sulfonyl, aminosulfonyl, sulfinyl, sulfonamido, sulfamoyl, sulfamoylamino, phosphenyl, spiro compound residues or bridged hydrocarbon residues.

12. A photographic element as claimed in claim 1, wherein at least one $R_4$ group is an electron-donating group with a Hammett sigma p value of zero or less.

13. A photographic element as claimed in claim 1, wherein at least one $R_4$ group is a carbonamido, aryloxy or alkyloxy group.

14. A photographic element as claimed in claim 1, wherein at least one of the $R_2$, $R_3$ and $R_4$ substituents includes an aqueous-solubilizing group.

15. A photographic element as claimed in claim 1, wherein at least one of the $R_2$, $R_3$ and $R_4$ substituents includes an aqueous-solubilizing group selected from carboxy, carboxyalkyl, sulfo, sulfoalkyl, phosphato, phosphatoalkyl, phosphono, phosphonoalkyl, carbonamido, sulfonamido, hydroxy and salts thereof.

16. A photographic element as claimed in claim 1, wherein said hydrazide compound has the formula:

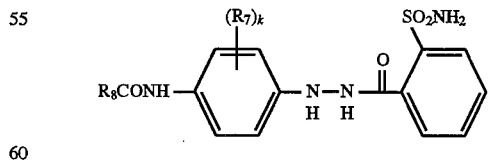

wherein
$R_7$=a substituent group
$R_8$=a ballasting group
k=1, 2, 3 or 4.

17. A photographic element comprising a support bearing at least one silver halide emulsion layer having associated therewith a hydrazide compound that functions as a scavenger for oxidized developing agent; said hydrazide compound having the formula:

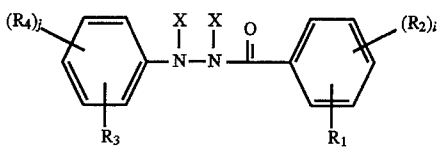

wherein:

each X is, independently, a hydrogen atom or a process-cleavable group;

$R_1$ is an electron-withdrawing and aqueous-solubilizing group selected from the group consisting of
—$SO_2NH_2$
—$SO_2NHC_6H_5$
—$CONHC_6H_5$
—$SO_2NHCOC_6H_5$
—$CONH_2$
—$SO_2NHCH_3$ and
—$CONHCH_3$;

each $R_2$ is, independently, a hydrogen atom or a monovalent organic substituent which is not an electron-donating group;

$R_3$ is a ballasting group;

each $R_4$ is, independently, a hydrogen atom or a monovalent organic substituent which is not an electron-withdrawing group;

i is an integer with a value of 1 to 4; and j is an integer with a value of 1 to 4.

18. A photographic element comprising a support bearing at least one silver halide emulsion layer having associated therewith a hydrazide compound that functions as a scavenger for oxidized developing agent, wherein said hydrazide compound has the formula:

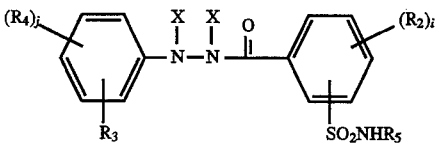

wherein:

$R_5$ is a hydrogen atom, or an acyl, alkyl or aromatic substituent;

each X is, independently, a hydrogen atom or a process-cleavable group;

each $R_2$ is, independently, a hydrogen atom or a monovalent organic substituent;

$R_3$ is a ballasting group;

each $R_4$ is, independently, a hydrogen atom or a monovalent organic substituent;

i is an integer with a value of 1 to 4; and j is an integer with a value of 1 to 4.

19. A photographic element comprising a support bearing at least one silver halide emulsion layer having associated therewith a hydrazide compound that functions as a scavenger for oxidized developing agent, wherein said hydrazide compound has the formula:

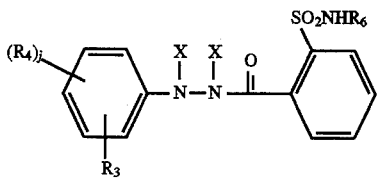

wherein:

$R_6$ is a hydrogen atom or an acyl substituent;

each X is, independently, a hydrogen atom or a process-cleavable group;

$R_3$ is a ballasting group;

each $R_4$ is, independently, a hydrogen atom or a monovalent organic substituent; and j is an integer with a value of 1 to 4.

20. A photographic element comprising a support and at least one silver halide emulsion layer and including:

(1) a four-equivalent 5-pyrazolone magenta-dye-forming coupler in reactive association with said silver halide emulsion layer; and (2) in reactive association with said coupler a hydrazide compound that functions as a scavenger for oxidized developing agent; said hydrazide compound having the formula:

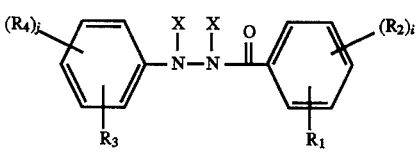

wherein each X is, independently, a hydrogen atom or a process-cleavable group;

$R_1$ is an electron-withdrawing and aqueous-solubilizing group;

each $R_2$ is, independently, a hydrogen atom or a monovalent organic substituent;

$R_3$ is a ballasting group;

each $R_4$ is, independently, a hydrogen atom or a monovalent organic substituent;

i is an integer with a value of 1 to 4; and j is an integer with a value of 1 to 4.

21. A photographic element as claimed in claim 20, wherein said four-equivalent 5-pyrazolone magenta-dye-forming coupler has the formula:

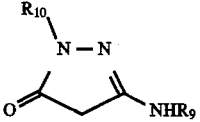

wherein $R_9$ and $R_{10}$ are, independently, a ballast group, an unsubstituted or substituted alkyl group, phenyl or substituted phenyl.

22. A photographic element as claimed in claim 20, wherein said four-equivalent 5-pyrazolone magenta-dye-forming coupler has the formula:

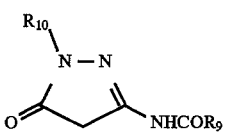

wherein $R_9$ and $R_{10}$ are, independently, a ballast group, an unsubstituted or substituted alkyl group, phenyl or substituted phenyl.

23. A multicolor photographic element comprising a support having thereon:
   (1) a blue-recording yellow-dye-image-forming layer unit;
   (2) a green-recording magenta-dye-image-forming layer unit; and
   (3) a red-recording cyan-dye-image-forming layer unit, each of said dye-image-forming layer units containing at least one silver halide emulsion layer comprised of a vehicle and silver halide grains and said element additionally comprising a scavenger for oxidized-color-developing agent; said scavenger being a hydrazide compound having the formula:

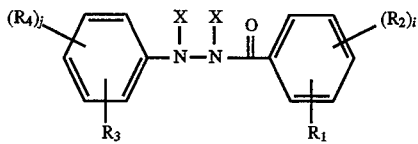

wherein
   each X is, independently, a hydrogen atom or a process-cleavable group;

$R_1$ is an electron-withdrawing and aqueous-solubilizing group;

each $R_2$ is, independently, a hydrogen atom or a monovalent organic substituent;

$R_3$ is a ballasting group;

each $R_4$ is, independently, a hydrogen atom or a monovalent organic substituent;

i is an integer with a value of 1 to 4; and j is an integer with a value of 1 to 4.

24. A photographic element comprising a support and at least one silver halide emulsion layer and including:
   (1) a four-equivalent 5-pyrazolone magenta-dye-forming coupler in reactive association with said silver halide emulsion layer; and
   (2) in reactive association with said coupler a hydrazide compound that functions as a scavenger for oxidized developing agent; said hydrazide compound having the formula:

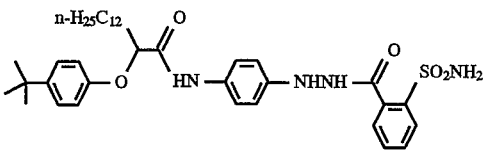

* * * * *